United States Patent
Tao et al.

(10) Patent No.: US 12,214,339 B2
(45) Date of Patent: Feb. 4, 2025

(54) NANOCAGE-CONFINED CATALYST, PREPARATION PROCESS AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Guiju Tao, Shanghai (CN); Weimin Yang, Shanghai (CN); Wenjun He, Shanghai (CN); Fengping Yu, Shanghai (CN); Shaoqing Jin, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 1039 days.

(21) Appl. No.: 17/265,178

(22) PCT Filed: Jul. 30, 2019

(86) PCT No.: PCT/CN2019/098304
§ 371 (c)(1),
(2) Date: Feb. 1, 2021

(87) PCT Pub. No.: WO2020/024923
PCT Pub. Date: Feb. 6, 2020

(65) Prior Publication Data
US 2021/0299644 A1      Sep. 30, 2021

(30) Foreign Application Priority Data

Jul. 31, 2018 (CN) .......................... 201810854835.1
Oct. 25, 2018 (CN) .......................... 201811251045.0
Oct. 25, 2018 (CN) .......................... 201811251064.3

(51) Int. Cl.
  *B01J 31/18*      (2006.01)
  *B01J 21/18*      (2006.01)
  (Continued)

(52) U.S. Cl.
  CPC .......... *B01J 31/1805* (2013.01); *B01J 21/18* (2013.01); *B01J 35/23* (2024.01); *B01J 37/0219* (2013.01);
  (Continued)

(58) Field of Classification Search
  CPC ............................. B01J 31/1805; B01J 35/23
  See application file for complete search history.

(56) References Cited

U.S. PATENT DOCUMENTS

2003/0032821 A1 * 2/2003 Kim ...................... C07F 15/065
                                                            556/32
2004/0054201 A1   3/2004 Kim et al.
2006/0069293 A1   3/2006 Van Hal et al.

FOREIGN PATENT DOCUMENTS

CN      100413579 C     8/2008
CN      102372815 A     3/2012
(Continued)

OTHER PUBLICATIONS

Salavati-Miasari. Ship-in-a-bottle synthesis, characterization and catalytic oxidation of cyclohexane by Host (nanopores of zeolite-Y) /guest (Mn(II), Co(II), Ni(II) and Cu(II) complexes of bis-(salicylaldehyde)oxaloyldihydrazone) nanocomposite materials. J Mol Catalysis A: Chemical 285 (2008) 58-67 (Year: 2008).*

(Continued)

*Primary Examiner* — Matthew E. Hoban
(74) *Attorney, Agent, or Firm* — NKL Law; Allen Xue

(57) ABSTRACT

A nanocage-confined catalyst has the formula: NC-m[M(Salen1)X]-n[M'(Salen2)]. NC is a material having a nanocage structure, and M(Salen1)X and M' (Salen2) are active centers, respectively; each occurrence of M is independently selected from the group consisting of Co ion, Fe
(Continued)

ion, Ga ion, Al ion, Cr ion, and a mixture thereof. Each occurrence of M' is independently selected from Cu ion, Ni ion and a mixture thereof, m is 0 to 100; n is 0 to 100, with the proviso that at least one of m and n is not 0; each occurrence of Salen1 and Salen2 is independently a derivative of Shiff bases; X is an axial anion selected from the group consisting of substituted or unsubstituted acetate, substituted or unsubstituted benzene sulfonate, substituted or unsubstituted benzoate, F—, Cl—, Br—, I—, SbF6-, PF6-, BF4-, and a mixture thereof.

19 Claims, 2 Drawing Sheets

(51) Int. Cl.
| | | |
|---|---|---|
| | *B01J 35/23* | (2024.01) |
| | *B01J 37/02* | (2006.01) |
| | *C07C 29/154* | (2006.01) |
| | *C07C 29/156* | (2006.01) |
| | *C07C 29/157* | (2006.01) |

(52) U.S. Cl.
CPC .......... *C07C 29/154* (2013.01); *C07C 29/156* (2013.01); *C07C 29/157* (2013.01); *B01J 2231/48* (2013.01); *B01J 2531/0252* (2013.01); *B01J 2531/16* (2013.01); *B01J 2531/31* (2013.01); *B01J 2531/32* (2013.01); *B01J 2531/62* (2013.01); *B01J 2531/842* (2013.01); *B01J 2531/847* (2013.01)

(56) References Cited

FOREIGN PATENT DOCUMENTS

| | | |
|---|---|---|
| CN | 102688776 A | 9/2012 |
| CN | 104437607 B | 6/2016 |
| CN | 109675627 A | 4/2019 |
| CN | 109675628 A | 4/2019 |
| CN | 109675629 A | 4/2019 |
| CN | 109675631 A | 4/2019 |
| JP | 2003534117 A | 11/2003 |

OTHER PUBLICATIONS

Sharma. Chiral Ni-Schiff Base Complexes inside Zeolite-Y and TheirApplication in Asymmetric Henry Reaction: Effect of Initial Activationwith Microwave Irradiation. J. Phys. Chem. C 2016, 120, 13563-13573 (Year: 2016).*
Zhong. Epoxides hydration on ColII(salen)-OTs encapsulated in silica nanocages modified with prehydrolyzed TMOS. Jounral of Calaysis 338 (2016) 184-191 (Year: 2016).*
Nielsen. Mechanistic Investigation Leads to a Synthetic Improvement in the Hydrolytic Kinetic Resolution of Terminal Epoxides. J. Am. Chem. Soc. 2004, 126, 1360-1362 (Year: 2004).*
Hailu. Synthesis, characterization and catalytic application of zeolite based heterogeneous catalyst of iron(III), nickel(II) and copper(II) salen complexes for oxidation of organic pollutants. J Porous Mater (2015) 22:1363-1373 (Year: 2015).*
Bania, Kusum K. et al.; "Enantioselective Henry Reaction Catalyzed by 'Ship in a Bottle' Complexes"; Inorganic Chemistry; vol. 52; Jul. 2, 2013; pp. 8017-8029.
Sharma, Mukesh et al.; "Chiral-Ni-Schiff Base Complexes Inside Zeolite-Y and Their Application in Asymmetric Henry Reaction: Effect of Initial Activation with Microwave Irradiation"; The Journal of Physical Chemistry C; Jun. 8, 2016; pp. 1-37.
Xavier, K.O et al.; "Zeolite-encapsulated Co(II), Ni(II) and Cu(II) complexes as catalysts for partial oxidation of benzyl alcohol and ethylbenzene"; Applied Catalysis A: General; vol. 258, Issue 2; Feb. 20, 2004; pp. 251-259; https://doi.org/10.1016/j.apcata.2003.09.027.
Choi, Sung-Dae et al.; Enantioselective hydrolytic kinetic resolution of epoxides catalyzed by chiral Co(III) salen complexes immobilized in the membrane reactor; Catalysis Letters, vol. 92, pp. 35-40, Dec. 31, 2004.
Li, Bo et al.: "Hydration of Epoxides on [ColII(salen)] Encapsulated in Silica-Based Nanoreactors"; Angewandte Chemie International Edition; vol. 51, Year: 2012, pp. 11517-11521.
Zhong, Mingmei et al.; "Epoxides hydration on ColII(salen)-OTs encapsulated in silica nanocages modified with brehydrolyzed TMOS", Journal of Catalysis, vol. 338, Mar. 24, 2016, pp. 184-191.
Li, Bo et al.; "Hydration of Epoxides on [Co III (salen)] Encapsulated in Silica-Based Nanoreactors"; Angewandte Chemie International Edition; vol. 51, No. 46; Nov. 12, 2012; pp. 11517-11521.
Gupta, K.C. et al.: "Catalytic activities of Schiff base transition metal complexes", Coordination Chemistry Reviews, vol. 252, No. 12-14; Jul. 1, 2008; pp. 1420-1450.

* cited by examiner

NANOCAGE-CONFINED CATALYST, PREPARATION PROCESS AND USE THEREOF

TECHNICAL FIELD

The invention relates to a nanocage-confined catalyst, a preparation process and use thereof.

BACKGROUND

Ethylene glycol, as an important raw material and an intermediate for organic chemical industry, is mainly used for producing polyester fibers, bottle resin, films, engineering plastics, antifreeze and coolant, and also used as a raw material for producing a large number of chemical products such as plasticizers, desiccants, lubricants and the like, with a very wide application (*Guangdong Chemical Industry*, 2011, 38: 242). By 2015, the global annual demand for ethylene glycol was as high as 28 million tons (http://www.shell.com/business-customers/chemicals/products-speeds-and-adhesives/products/mono-ethylene-glycol.html). At present, ethylene glycol is mainly produced by a direct hydration process of ethylene oxide in industry. In order to reduce the content of by-products such as diethylene glycol and triethylene glycol, the technique requires that the reaction is carried out at 190-200° C., more than 1.9 MPa and a feed molar ratio of water to ethylene oxide (called as water ratio) of 22-25:1, so that the water content in the product is up to 85 wt. %. To remove such a large amount of water, a multi-effect evaporation system is required and a large amount of steam is consumed (e.g., 5.5 tons of steam are consumed for producing 1 ton of ethylene glycol when the water ratio is 20:1), which ultimately results in a large energy consumption, complicated equipment, long process flow, and high production cost for the whole preparation process of ethylene glycol (*Industrial Catalysis*, 2002, 10: 3; petrochemical, 2010, 39: 562; *Chemical Intermediate*, 2009: 59). Therefore, the development of the ethylene oxide catalytic hydration technology with low water ratio is expected to realize energy conservation and consumption reduction, and the core is the development of the catalyst.

Heretofore, various catalysts have been developed, such as anion/cation exchange resins (CN 102372815B; *Journal of Applied Polymer Science*, 2010, 115: 2946; *RSC Advances*, 2015, 5: 2550), supported metal oxides (CN 100413579C; *Journal of Catalysis*, 2006, 241: 173), Sn zeolites (CN 104437607B; *ACS Catalysis*, 2016, 6: 2955), and the like. However, these catalysts still require a high water ratio (≥8:1) or a long reaction time (≥24 h) for good catalytic performance. In a recent breakthrough progress, the nanocage catalyst FDU-12-[Co(Salen) X] (X=OAc⁻/OTs⁻) (CN201110070058. X; *Angewandte Chemie International Edition*, 2012, 51: 11517; Journal of Catalysis, 2016, 338: 184) developed by Dalian Institute of Chemical Physics can obtain ethylene glycol with a yield of more than 98% at a water ratio of 2:1. However, FDU-12-[Co(Salen)X] (X=OAc⁻/OTs⁻) has poor stability, which needs to be activated for good recycling property and severely limits the industrial application. Therefore, there is a strong need in the art to develop a catalyst having high activity for the hydration of alkylene oxide to produce glycol at a low water ratio and a short reaction time and having good recyclability without activation.

SUMMARY OF THE INVENTION

The invention aims to provide a catalyst having high activity and good recycling performance without activation for producing glycol by hydrating alkylene oxide under both high and low water ratios and short reaction time, and a process of preparing same, so as to solve the problems that the catalyst for producing glycol by hydrating alkylene oxide in the prior art needs high water ratio and can have good recycling performance only after activation. The catalyst provided by the invention has high activity for producing glycol by hydrating alkylene oxide under both high and low water ratios and short reaction time, and has good recycling performance without activation; the preparation process provided by the invention is simple and feasible, and can provide reference for the synthesis of other nanocage-confined catalysts.

In a first aspect, the present invention provides a nanocage-confined catalyst, having a formula of:

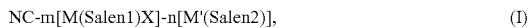

$$NC\text{-}m[M(Salen1)X]\text{-}n[M'(Salen2)], \quad (I)$$

wherein NC is a material having a nanocage structure, and the sub-formula (I-1), M(Salen1)X, and the sub-formula (I-2), M'(Salen2), are active centers, respectively; each occurrence of M is independently selected from the group consisting of Co ion, Fe ion, Ga ion, Al ion, Cr ion, and a mixture thereof; each occurrence of M' is independently selected from the group consisting of Cu ion, Ni ion and a mixture thereof; m is 0 to 100; n is 0 to 100, with the proviso that at least one of m and n is not 0; each occurrence of Salen1 and Salen2 is independently a derivative of the class of Shiff bases; x is an axial anion, selected from the group consisting of substituted or unsubstituted acetate, substituted or unsubstituted benzene sulfonate, substituted or unsubstituted benzoate, a halide anion (e.g., F⁻, Cl⁻, Br⁻, I⁻, SbF₆⁻, PF₆⁻, BF₄⁻, and a mixture thereof.

In one embodiment, each occurrence of M is independently selected from Fe³⁺, Ga³⁺, Al³⁺, Cr³⁺ and a mixture thereof.

In one embodiment, each occurrence of M' is independently selected from Cu²⁺, Ni²⁺, and a mixture thereof.

According to the invention, m and n are integers, indicating the number of categories of the active center in the sub-formulas (I-1) and (I-2) of the catalyst. For example, in one embodiment, the catalyst can be NC-2[M(Salen1)X]-1[M'(Salen2)], which means that the catalyst is formed from 2 different categories of active centers of formula (I-1) combined with 1 category of active center of formula (I-2), such as NC-1[Fe(Salen1)OAc]-1[Ga(Salen1)OTs]-1[Cu(Salen2)], indicating that 3 categories of active centers respectively with the structures of [Fe(Salen1)OAc], [Ga(Salen1)OTs], and [Cu(Salen2)] are used together. For another example, in one embodiment, the catalyst may be NC-1[Ga(Salen1)SbF₆]-1[Al(Salen1)Cl]-0[Cu(Salen2)], indicating that [Ga(Salen1)SbF₆] and [Al(Salen1)Cl] are used together; accordingly, the catalyst may be collectively represented as NC-[Ga(Salen1)SbF₆]—[Al(Salen1)Cl].

According to the invention, the ratio of the amount of active centers of sub-formula (I-1) to that of sub-formula (I-2) in the catalyst of formula (I) is not particularly restricted. In one embodiment, the molar ratio of the active centers between sub-formulas (I-1) and (I-2) is in the range of from 0.001 to 1000, such as from 0.01 to 100, or from 0.1 to 10, or from 0.5 to 5.

In one embodiment, m is from 0 to 20, preferably from 0 to 10, or preferably from 0 to 5, for example from 0 to 2.

In one embodiment, n is from 0 to 10, preferably from 0 to 5, or preferably from 0 to 3, for example from 0 to 1.

In one embodiment, m is 0 to 2, and n is 0 to 1. In a preferred embodiment, m is 2, n is 0 to 1, and each occurrence of M(Salen1)X is same or different. In a preferred embodiment, m is 2, n is 0, and each occurrence of M(Salen1)X is same or different.

In the embodiment above, when m is 2 or more, M(Salen1)X in each occurrence of (I-1) is independently same or different.

In the embodiment above, when n is 2 or more, M'(Salen2) in each occurrence of (I-2) is independently same or different.

In one embodiment, m is 1, n is 0, M is not Co, and X is not a halogen; and when m is 2, at least one X is $SbF_6^-$, and preferably, another X is $F^-$, $Cl^-$, $Br^-$ or $I^-$.

In one embodiment, preferably, the NC represents mesoporous silica nanoparticles having a nanocage structure or organic hybrid mesoporous silica nanoparticles having a nanocage structure.

In one embodiment, preferably, the NC includes SBA-6, SBA-16, FDU-1, FDU-12, KIT-5, AMS-8, and the like.

In one embodiment, preferably, the Shiff base derivative is N,N'-disalicylidene-1,2-cyclohexanediamine or a substituted N,N'-disalicylidene-1,2-cyclohexanediamine, such as (1R,2R)—N,N'-disalicylidene-1,2-cyclohexanediamine or a substituted (1R,2R)—N, N'-disalicylidene-1,2-cyclohexanediamine.

In a first exemplary variant of the nanocage-confined catalyst according to the first aspect of the invention, the catalyst may have formula (I-3) or (I-4) of:

NC-[M(Salen1)X]     (I-3), or

NC-[M'(Salen2)]     (I-4);

wherein, M(Salen1)X and M'(Salen2) are respectively active centers, in which M and M' are metal ion, where M comprises $Fe^{3+}$, $Ga^{3+}$, $Al_3^+$ and $Cr^{3+}$, and M' comprises $Cu^{2+}$ and $Ni^{2+}$, X is an axial anion, and Salen1 and Salen2 have the same definition as the Salen1 and Salen2 in the first aspect, namely, being Shiff base derivatives.

In one embodiment of the above first exemplary variant, preferably, X comprises acetate, benzenesulfonate, benzoate, substituted acetate, substituted benzenesulfonate, and substituted benzoate.

In a second exemplary variant of the nanocage-confined catalyst according to the first aspect of the invention, the catalyst may have formula (II-2) of:

NC-[M(Salen1)$SbF_6$-M(Salen1)X]     (II-2);

wherein M(Salen1)$SbF_6$-M(Salen1)X is an active center, M is a metal ion, Salen1 is a Shiff base derivative, X is an axial anion, and X is a halide anion.

In one embodiment of the second exemplary variant above, preferably, M comprises $Co^{3+}$, $Fe^{3+}$, $Ga^{3+}$, $Al^{3+}$, $Cr^{3+}$.

In one embodiment of the second exemplary variant above, preferably, the halide anion is $F^-$, $Cl^-$, $Br^-$, or $I^-$.

In a third exemplary variant of the nanocage-confined catalyst according to the first aspect of the invention, the catalyst may have formula (III) of:

NC-[M(Salen1)X]     (III)

wherein M(Salen1)X is an active center, M is a metal ion, M comprises $Co^{3+}$, $Fe^{3+}$, $Ga^{3+}$, $Al^{3+}$, and $Cr^{3+}$, Salen is a Shiff base derivative, X is an axial anion, and X is $PF_6^-$, or $BF_4^-$.

In one embodiment of the third exemplary variant above, Salen1 has the same definition as Salen1 or Salen2 described in the first aspect.

In a fourth exemplary variant of the nanocage-confined catalyst according to the first aspect of the invention, the catalyst may have formula (II-3) of:

NC—[Co(Salen1)$SbF_6$-M(Salen1)X]     (II-3),

In formula (II-3), M is a metal ion, NC and Salen1 each independently have the same definition as in one of the embodiments according to the foregoing first aspect and the first to the third exemplary variants, and X is a halide anion.

In one embodiment of the above fourth exemplary variant, preferably, M comprises $Co^{3+}$, $Fe^{3+}$, $Ga^{3+}$, $Al^{3+}$, and $Cr^{3+}$.

In one embodiment of the above fourth exemplary variant, preferably, the halide anion is $F^-$, $Cl^-$, $Br^-$, or $I^-$.

In a fifth exemplary variant of the nanocage-confined catalyst according to the first aspect of the invention, the catalyst may have formula (II-4) of:

NC-[M(Salen1)$SbF_6$—Co(Salen1)X]     (II-4),

In formula (II-4), M is a metal ion, NC and Salen1 each independently have the same definition as in one of the embodiments according to the foregoing first aspect and the first to the fourth exemplary variants, and X is a halide anion.

In one embodiment of the fifth exemplary variant above, preferably, M comprises $Co^{3+}$, $Fe^{3+}$, $Ga^{3+}$, $Al^{3+}$, and $Cr^{3+}$.

In one embodiment of the fifth exemplary variant above, preferably, the halide anion is $F^-$, $Cl^-$, $Br^-$, or $I^-$.

In a sixth exemplary variant of the nanocage-confined catalyst according to the first aspect of the present invention, the nanocage-confined catalyst of the present invention may have formula (III-1) or (III-2):

NC—[Co(Salen1)$PF_6$]     (III-1) or

NC—[Co(Salen1)$BF_4$]     (III-2), wherein NC and Salen1 each independently have the same definitions as in one of the embodiments according to the aforementioned first aspect and the each exemplary variant thereof.

In each of the exemplary variants according to the first aspect of the invention above, the active center, NC, M, Salen1, Salen2, X, m, n and the like involved have the same meaning as defined in the first aspect, unless otherwise specified in each exemplary variant.

The second aspect of the invention also provides a process of preparing the nanocage-confined catalyst, comprising the steps of:

adding an active center, M(Salen1)X or M'(Salen2), and nanocage material NC into a solvent, and stirring; removing the solvent; and encapsulating, to obtain the nanocage-confined catalyst;

wherein M, M', Salen1 or Salen2, X and NC each independently have the same definition as in one of the embodiments according to the aforementioned first aspect and the each exemplary variant thereof.

In one embodiment, the preparation process of the second aspect of the invention may be used to prepare nanocage-confined catalysts according to the first aspect of the invention and each of the exemplary variants thereof.

In the above technical solution, preferably, the solvent includes at least one of dichloromethane, ethanol and methanol.

In the above technical solution, stirring and removing the solvent are preferably conducted at a temperature of −96° C. to 61° C., more preferably, 20-50° C. In an exemplary embodiment, the duration for stirring is 30 min or more. In an exemplary embodiment, the solvent is removed by volatilizing the solvent with exposure to the ambient under stirring.

In the above technical solution, preferably, the encapsulation is conducted with an encapsulating agent. In one embodiment, in particular, encapsulation of the active centers is achieved with prehydrolyzed methyl orthosilicate or prehydrolyzed ethyl orthosilicate or a silane coupling agent.

The third aspect of the invention further provides use of the catalyst above or the catalyst prepared by the preparation process above in the reaction of producing glycol by hydration of alkylene oxide.

The conditions for the use comprise: a water ratio of ≥2:1, a reaction time of 10 min-24 h, and a yield of ethylene glycol or propylene glycol obtained by the hydration reaction of ethylene oxide or propylene oxide catalyzed for the first-through is ≥91%, preferably ≥93%; a yield of the ethylene glycol or the propylene glycol obtained by directly recycling the catalyst above for 1 time without activation regeneration is ≥75%, preferably ≥90%; and a yield of the ethylene glycol or the propylene glycol obtained by directly recycling the catalyst above for 2 times without activation regeneration is ≥64%, preferably ≥83%, and further preferably ≥84%.

The catalyst according to the present invention comprises a substrate material containing a nanocage structure and an active center of M(Salen1)X or M'(Salen2) confined in the nanocage, wherein M is $Co^{3+}$, $Fe^{3+}$, $Ga^{3+}$, $Al^{3+}$, or $Cr^{3+}$, M' is $Cu^{2+}$ or $Ni^{2+}$, Salen1 and Salen2 are Shiff base derivatives, and X is an axial anion. The process provided by the invention is simple and feasible, and provides reference for the synthesis of other nanocage-confined catalysts. The catalyst has high activity and good recycling performance without activation for producing glycol by hydrating alkylene oxide under both high and low water ratios and short reaction time, and good stability, which represent unexpected effects. The preparation process provided by the invention is simple and feasible, and can provide reference for the synthesis of other nanocage-confined catalysts.

DRAWINGS

EMBODIMENTS

Figure 1:
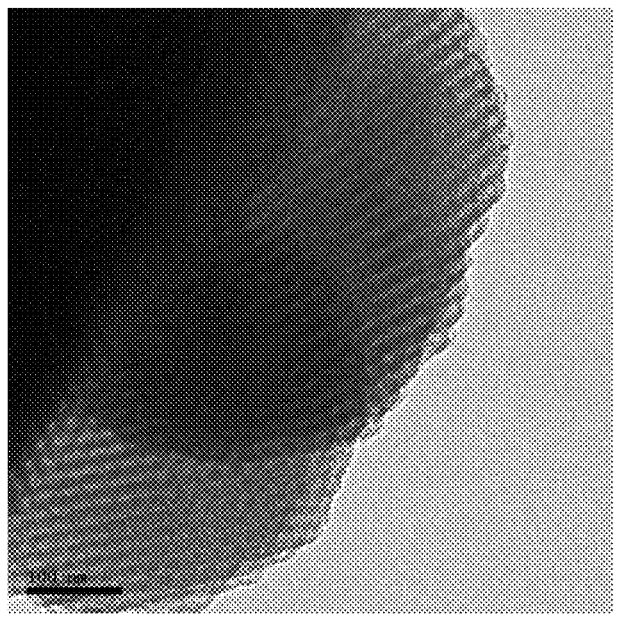
FIG. 1 is a TEM photograph of the catalyst obtained in example I-1.
Figure 2:
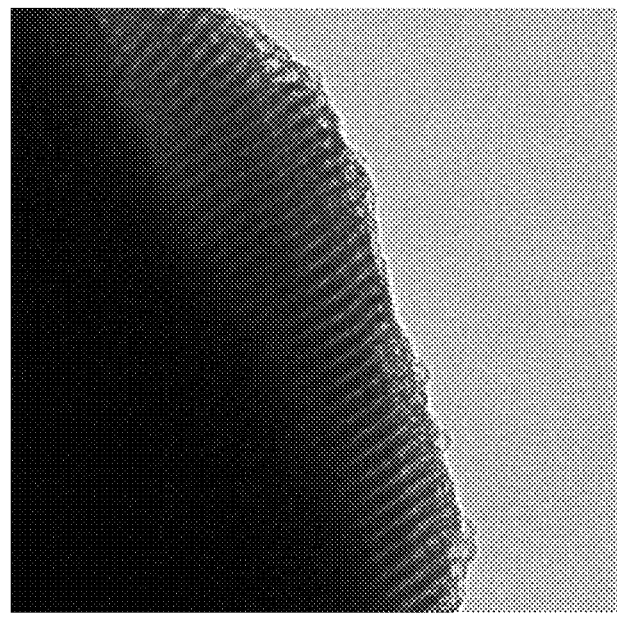
FIG. 2 is a TEM photograph of the catalyst obtained in example II-1.
Figure 3:
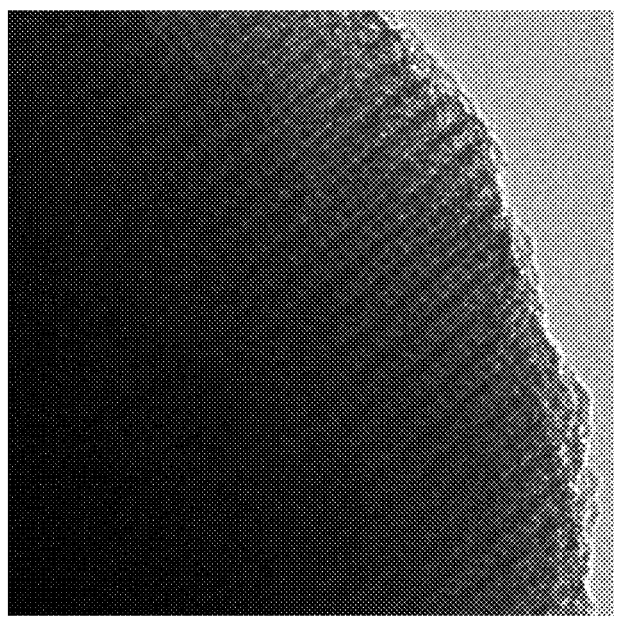
FIG. 3 is a TEM photograph of the catalyst obtained in example III-1.

The present invention will be further illustrated in more detail below, while it should be understood that the scope of the invention is not restricted by the embodiments, but is defined by the appended claims.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

All ranges involved herein are inclusive of their endpoints unless specifically stated otherwise. Further, when a range, one or more preferred ranges, or a plurality of preferable upper and lower limits, are given for an amount, concentration, or other value or parameter, it is to be understood that all ranges formed from any pair of any upper limit or preferred values thereof and any lower limit or preferred values thereof are specifically disclosed, regardless of whether such pairs of values are individually disclosed.

All percentages, parts, ratios, etc. involved in this specification are indicated by weight unless explicitly stated otherwise, unless the basis on weight does not conform to the conventional understanding by those skilled in the art.

"Ranges" as disclosed herein are given with lower and upper limits, e.g., one or more lower limits and one or more upper limits. A given range may be defined by selecting a lower limit and an upper limit that define the boundaries of the given range. All ranges defined in this manner are inclusive and combinable, i.e., any lower limit may be combined with any upper limit to form a range. For example, ranges of 60-110 and 80-120 are listed for particular parameters, meaning that ranges of 60-120 and 80-110 are also contemplated. Furthermore, if the lower limits listed are 1 and 2 and the upper limits listed are 3, 4 and 5, then the following ranges are all contemplated: 1-3, 1-4, 1-5, 2-3, 2-4, and 2-5.

In this context, unless otherwise stated, a numerical range "a-b" represents an abbreviation for any combination of real numbers between a and b, where a and b are both real numbers. For example, a numerical range of "0 to 5" indicates that all real numbers between "0 to 5" have been listed herein, and "0 to 5" is simply an abbreviated representation of the combination of these numbers.

In this context, the ranges of the contents of the individual components of the composition and their preferred ranges can be combined with one another to form new technical solutions, unless stated otherwise.

As used herein, unless otherwise indicated, the total amount of each component in percentages for all compositions add up to 100%.

All embodiments and preferred embodiments mentioned herein can be combined with each other to form new technical solutions, unless otherwise stated.

All the technical features mentioned herein, as well as preferred features, can be combined with each other to form new technical solutions, unless stated otherwise.

In this context, all steps mentioned herein may be performed sequentially or randomly, but preferably sequentially, unless otherwise indicated. For example, the process comprises steps (a) and (b), meaning that the process may comprise steps (a) and (b) performed sequentially, and may also comprise steps (b) and (a) performed sequentially. For example, reference to the process further comprising step (c) means that step (c) may be added to the process in any order, for example, the process may comprise steps (a), (b) and (c), may also comprise steps (a), (c) and (b), may also comprise steps (c), (a) and (b), etc.

In this document, unless otherwise indicated, the terms "comprising," "including," "contain", "having," and similar words are to be construed as open-ended, but should also be construed to cover closed-ended situations as if all such situations were explicitly set forth. For example, "comprising" means not only the case where other elements not listed may be included, but also the case where only the listed elements are included. Furthermore, as used herein, "including/comprising" is interpreted as specifying the presence of the stated features, integers, steps or components as referred to, but does not preclude the presence or addition of one or more other features, integers, steps, components or groups thereof. Additionally, the term "comprising" is intended to include embodiments encompassed by the terms "consisting essentially of . . . " and "consisting of . . . ". Similarly, the term "consisting essentially of . . . " is intended to include embodiments encompassed by the term "consisting of . . . ".

In this context, unless stated otherwise, specific steps, specific values and specific substances mentioned in the Examples may be combined with other features in other parts of the description. For example, where the Summary or Embodiment section of the specification refers to a reaction temperature of 10 to 100° C. and the examples describe a specific reaction temperature of 20° C., it is to be understood that the range of 10 to 20° C. or the range of 20 to 100° C. has been specifically disclosed herein and may be combined with other features in other sections of the specification to form new embodiments.

According to the invention, for example, the following exemplary embodiments are provided:

1.1. A nanocage-confined catalyst, characterized in that the catalyst is represented by the formula: NC-[M(Salen)X] or NC-[M'(Salen)], wherein NC is a material having a nanocage structure; M(Salen)X and M'(Salen) are active centers, in which M and M' are metal ion, M comprises $Fe^{3+}$, $Ga^{3+}$, $Al^{3+}$, and $Cr^{3+}$, M' comprises $Cu^{2+}$ and $Ni^{2+}$, Salen is a Shiff base derivative, and X is an axial anion.

1.2 The catalyst according to the exemplary embodiment 1.1, characterized in that X comprises acetate, benzenesulfonate, benzoate, substituted acetate, substituted benzenesulfonate, and substituted benzoate.

1.3. The catalyst according to the exemplary embodiment 1.1, characterized in that NC is mesoporous silica nanoparticles having a nanocage structure or organic hybrid mesoporous silica nanoparticles having a nanocage structure.

1.4 The catalyst according to the exemplary embodiment 1.1, characterized in that the NC comprises SBA-6, SBA-16, FDU-1, FDU-12, KIT-5, and AMS-8.

1.5 The catalyst according to the exemplary embodiment 1.1, characterized in that the Shiff base derivative is N,N'-disalicylidene-1,2-cyclohexanediamine or a substituted N, N'-disalicylidene-1, 2-cyclohexanediamine.

1.6 A process of preparing a nanocage-confined catalyst, comprising the steps of:
adding an active center of M(Salen)X or M'(Salen) and nanocage material NC into a solvent, and stirring; removing the solvent; and encapsulating, to obtain the nanocage-confined catalyst.

1.7 The process according to the exemplary embodiment 1.6, characterized in that M comprises $Fe^{3+}$, $Ga^{3+}$, $Al^{3+}$, and $Cr^{3+}$, M' comprises $Cu^{2+}$ and $Ni^2$; Salen is a Shiff base derivative, X is an axial anion, and the X comprises acetate, benzene sulfonate, benzoate, substituted acetate, substituted benzene sulfonate and substituted benzoate.

1.8 The process according to the exemplary embodiment 1.6, characterized in that the solvent comprises at least one of dichloromethane, ethanol, and methanol.

1.9 The process according to the exemplary embodiment 1.6, characterized in that the stirring and removing solvent are conducted at a temperature of −96° C. to 61° C.

1.10 A catalyst according to any one of the exemplary embodiments 1.1 to 1.5, or a catalyst obtained by the process according to any one of the exemplary embodiments 1.6 to 1.9 in a reaction of producing a glycol by hydration of an alkylene oxide.

2.1. A high performance nanocage-confined catalyst, characterized in that the catalyst has a formula of: NC-[M(Salen)$SbF_6$]. M(Salen) X], wherein NC is a material having a nanocage structure; M(Salen)$SbF_6$. M(Salen)X is an active center, in which M is a metal ion, Salen is a Shiff base derivative, and X is an axial anion and X is a halide anion.

2.2 The catalyst according to the exemplary embodiment 2.1, characterized in that M independently comprises $Co^{3+}$, $Fe^{3+}$, $Ga^{3+}$, $Al^{3+}$, and $Cr^{3+}$.

2.3. The catalyst according to the exemplary embodiment 2.1, characterized in that NC is mesoporous silica nanoparticles having a nanocage structure or organic hybrid mesoporous silica nanoparticles having a nanocage structure, preferably, NC comprises SBA-6, SBA-16, FDU-1, FDU-12, KIT-5, and AMS-8.

2.4. The catalyst according to the exemplary embodiment 2.1, characterized in that the Shiff base derivative is N,N'-disalicylidene-1, 2-cyclohexanediamine or a substituted N,N'-disalicylidene-1, 2-cyclohexanediamine.

2.5 The catalyst according to the exemplary embodiment 2.1, characterized in that the halide anion is $F^-$, $Cl^-$, $Br^-$, or $I^-$.

2.6, A process of preparing a nanocage-confined catalyst comprising the steps of:
adding active centers M(Salen)$SbF_6$ and M(Salen)X, and nanocage material NC into a solvent, and stirring; removing the solvent; and encapsulating, to obtain the nanocage-confined catalyst.

2.7 The process according to the exemplary embodiment 2.6, characterized in that the solvent comprises at least one of dichloromethane, ethanol, and methanol.

2.8 The process according to the exemplary embodiment 2.6, characterized in that the stirring and removing solvent are conducted at a temperature of −96° C. to 61° C.

2.9. The process according to the exemplary embodiment 2.6, characterized in that M is a metal ion, and M comprises $Co^{3+}$, $Fe^{3+}$, $Ga^{3+}$, $Al^{3+}$, and $Cr^{3+}$, Salen is a Shiff base derivative, X is an axial anion, and X is a halide anion.

2.10 Use the catalyst according to any one of the exemplary embodiments 2.1 to 2.5 or a catalyst obtained by the process according to any one of the exemplary embodiments 2.6 to 2.9 in a reaction for producing glycol by hydration of alkylene oxide.

3.1. A catalyst for producing glycol by hydration of alkylene oxide, characterized in that the catalyst is a nanocage-confined catalyst having a formula of: NC-[M(Salen)X], wherein M(Salen)X is confined in NC, and NC is a material having a nanocage structure; M(Salen)X is an active center, M is metal ion, and M comprises $Co^{3+}$, $Fe^{3+}$, $Ga^{3+}$, $Al^{3+}$, and $Cr^{3+}$, Salen is a Shiff base derivative, X is an axial anion, and X is $PF_6^-$ or $BF_4^-$.

3.2. The catalyst according to the exemplary embodiment 3.1, characterized in that NC is mesoporous silica nanoparticles having a nanocage structure or organic hybrid mesoporous silica nanoparticles having a nanocage structure.

3.3 The catalyst according to the exemplary embodiment 3.1, characterized in that the NC comprises SBA-6, SBA-16, FDU-1, FDU-12, KIT-5, and AMS-8.

3.4. The catalyst according to the exemplary embodiment 3.1, characterized in that the Shiff base derivative is N,N'-disalicylidene-1, 2-cyclohexanediamine or a substituted N, N'-disalicylidene-1, 2-cyclohexanediamine.

3.5 A process of preparing a catalyst for producing glycol by hydrating alkylene oxide, comprising the steps of:
dispersing an active center M(Salen)X and nanocage material NC into a solvent, stirring; removing the solvent; and adding an encapsulating agent for encapsulating, to obtain the nanocage-confined catalyst.

3.6 The process according to the exemplary embodiment 3.5, characterized in that the solvent comprises at least one of dichloromethane, ethanol, and methanol.

3.7 The process according to the exemplary embodiment 3.5, characterized in that the stirring and removing solvent are conducted at a temperature of −96° C. to 61° C.

3.8 The process according to the exemplary embodiment 3.5, characterized in that M is a metal ion, and M comprises $Co^{3+}$, $Fe^{3+}$, $Ga^{3+}$, $Al^{3+}$, and $Cr^{3+}$, Salen is a Shiff base derivative, X is an axial anion, and X comprises $PF_6^-$ and $BF_4^-$.

3.9 The process according to the exemplary embodiment 3.5, characterized in that the solvent is removed by volatilizing the solvent through exposure to ambient under stirring 3.10 Use of a catalyst according to any one of the exemplary embodiments 3.1 to 3.4, or a catalyst prepared by the process according to any one of the exemplary embodiments 3.5 to 3.9 in a reaction of producing glycol by hydrating alkylene oxide.

EXAMPLES

Example I-1

0.50 g of F127, 0.6 g of mesitylene and 2.5 g of KCl were weighed and dissolved in 30 mL of 2M HCl aqueous solution at a temperature of 16° C., and stirred for 2 hours; 2.08 g TEOS was added, stirring was continued for 24 h at 16° C. and then hydrothermal treatment was carried out in an oven at 100° C. for 24 h, taken out, washed, dried, and calcinated at 550° C. for 6 h to obtain the nanocage substrate material FDU-12. 0.2 g of p-toluenesulfonic acid monohydrate and 0.490 g of Fe (N,N'-disalicylidene-1,2-cyclohexanediamine) were weighed, dissolved in 20 mL of dichloromethane, and stirred at room temperature for 12 h with exposure to the ambient, solvent was removed by spinning, and fully washed with n-hexane and dried, to obtain the active center Fe(N,N'-disalicylidene-1,2-cyclohexanediamine)OTs. 1.0 g of FDU-12 was weighed and placed in 4 mL of dichloromethane solution containing 100 mg of Fe(N,N'-disalicylidene-1,2-cyclohexanediamine)OTs, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst I-A.

Example I-2

1.0 g of SBA-6 was weighed and placed in 4 mL of a mixed solution of 300 mg Ga(N,N'-bis(3,5-di-tert-butylsalicylidene)-1,2-cyclohexanediamine) OAc in ethanol and dichloromethane, sealed and stirred at 20° C. for 3 hours, and then stirred with exposure to the ambient at 40° C., until the solvent was evaporated out. Prehydrolyzed methyl orthosilicate was added, and stirred for 60 min. Ethanol was added, centrifugally separated, fully washed, and dried to obtain catalyst I-B.

Example I-3

1.0 g of SBA-16 was weighed and placed in 6 mL of a methanol solution containing 400 mg of Al (N,N'-disalicylidene-1,2-cyclohexanediamine)OAc, sealed and stirred at 20° C. for 4 h, and then stirred with exposure to the ambient at 30° C. until the solvent was evaporated out. Prehydrolyzed methyl orthosilicate was added, and stirred for 60 min. Ethanol was added, centrifugally separated, fully washed, and dried to obtain catalyst I-C.

Example I-4

1.0 g of FDU-1 was weighed into 6 mL of a mixed solution of methanol and ethanol containing 500 mg of Cr(N,N'-bis(3-di-tert-butylsalicylidene)-1,2-cyclohexanediamine)OAc, sealed and stirred at 30° C. for 4 h, and then stirred with exposure to the ambient at 40° C. until the solvent was evaporated out. 2 mL of toluene, 2 mg of p-toluenesulfonic acid and 20 mmol of trimethoxypropylsilane were added, refluxed overnight, centrifugally separated, fully washed, and dried to obtain the catalyst I-D.

Example I-5

1.0 g of KIT-5 was weighed and placed in 8 mL of an ethanol solution containing 600 mg of Cu(N,N'-bis(3-tert-butylsalicylidene)-1,2-cyclicethylenediamine), sealed and stirred at 30° C. for 3 h, and then stirred with exposure to the ambient at 50° C. until the solvent was evaporated. 2 mL of toluene, 2 mg of p-toluenesulfonic acid and 20 mmol of trimethoxypropylsilane were added, refluxed overnight, centrifugally separated, fully washed, and dried to obtain the catalyst I-E.

Example I-6

1.0 g of AMS-8 was weighed and placed in 10 mL of ethanol solution containing 700 mg of Ni (N,N'-bis(5-tert-butylsalicylidene)-1,2-cyclohexanediamine), sealed and stirred at 30° C. for 3 h, and then stirred with exposure to the ambient at 50° C. until the solvent was evaporated out. 2 mL of toluene, 2 mg of p-toluenesulfonic acid and 20 mmol of trimethoxypropylsilane were added, refluxed overnight, centrifugally separated, fully washed, and dried to obtain the catalyst I-F.

Comparative Example I-1

1.0 g of SBA-16 was weighed and placed in 6 mL of methanol solution containing 400 mg Co(N,N'-disalicylidene-1,2-cyclohexanediamine)OTs, sealed and stirred for 4 h at 20° C., and then stirred with exposure to the ambient at 30° C. until the solvent was evaporated out. Prehydrolyzed methyl orthosilicate was added, and stirred for 60 min. Ethanol was added, centrifugally separated, fully washed, and dried to obtain the catalyst I-G.

Example I-7

1.32 g of ethylene oxide was weighed, and the performance of catalyst I-A was evaluated under the condition of a temperature of 20° C., a pressure of 1.0 MPa, a water ratio of 2:1, a catalyst to ethylene oxide weight ratio of 1:1000 and a reaction duration of 7 hours. The results were shown in Table I-1.

Example I-8

The catalyst having been used once was recovered from example I-7, and was evaluated for its catalytic performance without activation regeneration under the same catalytic conditions as in example I-7. The results were shown in Table I-1.

Example I-9

The catalyst having been used twice was recovered from example I-8, and was evaluated for its catalytic performance without activation regeneration under the same catalytic conditions as in examples I-7 and I-8. The results were shown in Table I-1.

Example I-10

1.32 g of ethylene oxide was weighed, and the performance of the catalyst I-B was evaluated under the condition of a temperature of 20° C., a pressure of 1.0 MPa, a water ratio of 2:1, a molar ratio of the catalyst to the ethylene oxide of 1:1000 and a reaction duration of 7 h. The results were shown in a table I-1.

Example I-11

The catalyst having been used once was recovered from example I-10, and was evaluated for its catalytic performance without activation regeneration under the same catalytic conditions as in example I-10. The results were shown in Table I-1.

Example I-12

The catalyst having been used twice was recovered from example I-11, and was evaluated for its catalytic performance without activation regeneration under the same catalytic conditions as in examples I-10 and 11. The results were shown in Table I-1.

Example I-13

1.32 g of ethylene oxide was weighed and the performance of catalyst I-C was evaluated under the condition of a temperature of 20° C., a pressure of 1.0 MPa, a water ratio of 2:1, a molar ratio of the catalyst to the ethylene oxide of 1:1000 and a reaction duration of 7 h. The results were shown in Table I-1.

Example I-14

The catalyst having been used once was recovered from example I-13, and was evaluated for its catalytic performance without activation regeneration under the same catalytic conditions as in example I-13. The results were shown in Table I-1.

Example I-15

The catalyst having been used twice was recovered from example I-14, and was evaluated for its catalytic performance without activation regeneration under the same catalytic conditions as in examples I-13 and 14. The results were shown in Table I-1.

TABLE I-1

Recycling performance of catalysts I-A, I-B and I-C

| Catalyst | Yield of ethylene glycol, first use (%) | Yield of ethylene glycol, 1 recycle (%) | Yield of ethylene glycol, 2 recycles (%) |
|---|---|---|---|
| I-A | 94 | 79 | 69 |
| I-B | 94 | 78 | 68 |
| I-C | 92 | 76 | 66 |

Example I-16

1.32 g of ethylene oxide was weighed, and the performance of the catalyst I-D was evaluated under the conditions of a temperature of 40° C., a pressure of 1.0 MPa, a water ratio of 6:1, a molar ratio of the catalyst to the ethylene oxide of 1:500 and a reaction duration of 4 h. The results were shown in a table I-2.

Example I-17

The catalyst having been used once was recovered from example I-16, and was evaluated for its catalytic performance without activation regeneration under the same catalytic conditions as in example I-16. The results were shown in Table I-2.

Example I-18

The catalyst having been used twice was recovered from example I-17, and was evaluated for its catalytic performance without activation regeneration under the same catalytic conditions as in examples I-16 and 17. The results were shown in Table I-2.

Example I-19

1.32 g of ethylene oxide was weighed, and the performance of the catalyst I-E was evaluated under the conditions of a temperature of 40° C., a pressure of 1.0 MPa, a water ratio of 6:1, a molar ratio of the catalyst to the ethylene oxide of 1:500 and a reaction duration of 4 h. The results were shown in a table I-2.

Example I-20

The catalyst having been used once was recovered from example I-19, and was evaluated for its catalytic performance without activation regeneration under the same catalytic conditions as in example I-19. The results were shown in Table I-2.

Example I-21

The catalyst having been used twice was recovered from example I-20, and was evaluated for its catalytic performance without activation regeneration under the same catalytic conditions as in examples I-19 and 20. The results were shown in Table I-2.

Example I-22

1.32 g of ethylene oxide was weighed, and the performance of the catalyst I-F was evaluated under the conditions of a temperature of 40° C., a pressure of 1.0 MPa, a water ratio of 6:1, a molar ratio of the catalyst to the ethylene oxide of 1:500 and a reaction duration of 4 h. The results were shown in a Table I-2.

Example I-23

The catalyst having been used once was recovered from example I-22, and was evaluated for its catalytic performance without activation regeneration under the same catalytic conditions as in example I-22. The results were shown in Table I-2.

Example I-24

The catalyst having been used twice was recovered from example I-23, and was evaluated for its catalytic performance without activation regeneration under the same catalytic conditions as in examples I-22 and 23. The results were shown in Table I-2.

TABLE I-2

Recycling Performance performance of catalysts I-d, I-E, and I-F

| Catalyst | Yield of ethylene glycol, first use (%) | Yield of ethylene glycol, 1 recycle (%) | Yield of ethylene glycol, 2 recycles (%) |
|---|---|---|---|
| I-D | 94 | 79 | 68 |
| I-E | 92 | 77 | 67 |
| I-F | 93 | 78 | 68 |

Example I-25

1.74 g of propylene oxide was weighed, and the performance of the catalyst I-D was evaluated under the conditions of a temperature of 40° C., a pressure of 1.0 MPa, a water ratio of 2:1, a molar ratio of the catalyst to the propylene oxide of 1:1000 and a reaction duration of 7 h. The results were shown in a table I-3.

Example I-26

The catalyst having been used once was recovered from example I-25, and was evaluated for its catalytic performance without activation regeneration under the same catalytic conditions as in example I-25. The results were shown in Table I-3.

Example I-27

The catalyst having been used twice was recovered from example I-26, and was evaluated for its catalytic performance without activation regeneration under the same catalytic conditions as in examples I-25 and 26. The results were shown in Table I-3.

Example I-28

1.74 g of propylene oxide was weighed, and the performance of the catalyst I-E was evaluated under the conditions of a temperature of 40° C., a pressure of 1.0 MPa, a water ratio of 2:1, a molar ratio of the catalyst to the propylene oxide of 1:1000 and a reaction duration of 7 h. The results were shown in a table I-3.

Example I-29

The catalyst having been used once was recovered from example I-28, and was evaluated for its catalytic performance without activation regeneration under the same catalytic conditions as in example I-28. The results were shown in Table I-3.

Example I-30

The catalyst having been used twice was recovered from example I-29, and was evaluated for its catalytic performance without activation regeneration under the same catalytic conditions as in examples I-28 and 29. The results were shown in Table I-3.

Example I-31

1.74 g of propylene oxide was weighed, and the performance of the catalyst I-F was evaluated under the conditions of a temperature of 40° C., a pressure of 1.0 MPa, a water ratio of 2:1, a molar ratio of the catalyst to the propylene oxide of 1:1000 and a reaction duration of 7 h. The results were shown in a table I-3.

Example I-32

The catalyst having been used once was recovered from example I-31, and was evaluated for its catalytic performance without activation regeneration under the same catalytic conditions as in example I-31. The results were shown in Table I-3.

Example I-33

The catalyst having been used twice was recovered from example I-32, and was evaluated for its catalytic performance without activation regeneration under the same catalytic conditions as in examples I-31 and 32. The results were shown in Table I-3.

TABLE I-3

Recycling performance of catalysts I-D, I-E, and I-F

| Catalyst | Yield of propylene glycol, first use (%) | Yield of propylene glycol, 1 recycle (%) | Yield of propylene glycol, 2 recycles (%) |
|---|---|---|---|
| I-D | 93 | 78 | 67 |
| I-E | 91 | 75 | 64 |
| I-F | 92 | 77 | 66 |

Example I-34

1.74 g of propylene oxide was weighed, and the performance of the catalyst I-A was evaluated under the conditions of a temperature of 40° C., a pressure of 1.0 MPa, a water ratio of 8:1, a molar ratio of the catalyst to the propylene oxide of 1:500 and a reaction duration of 4 h. The results were shown in a table I-4.

Example I-35

The catalyst having been used once was recovered from example I-34, and was evaluated for its catalytic performance without activation regeneration under the same catalytic conditions as in example I-34. The results were shown in Table I-4.

Example I-36

The catalyst having been used twice was recovered from example I-35, and was evaluated for its catalytic performance without activation regeneration under the same catalytic conditions as in examples I-34 and 35. The results were shown in Table I-4.

Example I-37

1.74 g of propylene oxide was weighed, and the performance of the catalyst I-B was evaluated under the conditions of a temperature of 40° C., a pressure of 1.0 MPa, a water ratio of 8:1, a molar ratio of the catalyst to the propylene oxide of 1:500 and a reaction duration of 4 h. The results were shown in a table I-4.

Example I-38

The catalyst having been used once was recovered from example I-37, and was evaluated for its catalytic performance without activation regeneration under the same catalytic conditions as in example I-37. The results were shown in Table I-4.

Example I-39

The catalyst having been used twice was recovered from example I-38, and was evaluated for its catalytic performance without activation regeneration under the same catalytic conditions as in examples I-37 and 38. The results were shown in Table I-4.

Example I-40

1.74 g of propylene oxide was weighed, and the performance of the catalyst I-C was evaluated under the conditions of a temperature of 40° C., a pressure of 1.0 MPa, a water ratio of 8:1, a molar ratio of the catalyst to the propylene oxide of 1:500 and a reaction duration of 4 h. The results were shown in a table I-4.

Example I-41

The catalyst having been used once was recovered from example I-40, and was evaluated for its catalytic performance without activation regeneration under the same catalytic conditions as in example I-40. The results were shown in Table I-4.

Example I-42

The catalyst having been used twice was recovered from example I-41, and was evaluated for its catalytic performance without activation regeneration under the same catalytic conditions as in examples I-40 and 41. The results were shown in Table I-4.

TABLE I-4

Recycling Performance performance of catalysts I-A, I-B, and I-C

| Catalyst | Yield of propylene glycol, first use (%) | Yield of propylene glycol, 1 recycle (%) | Yield of propylene glycol, 2 recycles (%) |
|---|---|---|---|
| I-A | 93 | 77 | 68 |
| I-B | 93 | 76 | 67 |
| I-C | 92 | 76 | 66 |

Comparative Example I-2

1.32 g of ethylene oxide was weighed, and the performance of the catalyst I-G was evaluated under the conditions of a temperature of 20° C., a pressure of 1.0 MPa, a water ratio of 2:1, a molar ratio of the catalyst to the ethylene oxide of 1:1000 and a reaction duration of 7 h. The results were shown in a table I-5.

Comparative Example I-3

The catalyst having been used once was recovered from comparative example I-2, and was evaluated for its catalytic performance without activation regeneration under the same catalytic conditions as in comparative example I-2. The results were shown in Table I-5.

TABLE I-5

Recycling performance of catalyst I-G

| Catalyst | Yield of ethylene glycol, first use (%) | Yield of ethylene glycol, 1 recycle (%) |
|---|---|---|
| I-G | 96 | 44 |

Example II-1

0.50 g of F127, 0.6 g of mesitylene and 2.5 g of KCl were weighed and dissolved in 30 mL of 2M HCl aqueous solution at a temperature of 16° C., and stirred for 2 hours; 2.08 g TEOS was added, stirring was continued for 24 h at 16° C. and then hydrothermal treatment was carried out in an oven at 100° C. for 24 h, taken out, washed, dried, and calcinated at 550° C. for 6 h to obtain the nanocage substrate material FDU-12. 0.344 g of silver hexafluoroantimonate and 0.492 g of Co(N,N'-disalicylidene-1, 2-cyclohexanediamine) were weighed and dissolved in 40 mL of dichloromethane, stirred for 12 hours in the dark with exposure to the ambient at room temperature, and suction filtration repeatedly with kieselguhr, and the filtrate was collected and dried by spinning to obtain the active center Co(N,N'-disalicylidene-1, 2-cyclohexanediamine)SbF$_6$. 1.0 g of Co(N,N'-disalicylidene-1, 2-cyclohexanediamine)OTs was dissolved in 40 ml of methylene chloride, placed in a separatory funnel and washed three times with 40 ml of saturated sodium chloride, and dried over sodium sulfate, so as to remove the solvent, and the resulting solid was suspended in pentane and filtered to obtain the active center Co(N, N'-disalicylidene-1, 2-cyclohexanediamine)Cl. 1.0 g of FDU-12 was weighed and placed in 4 mL of dichloromethane solution containing 40 mg of Co(N,N'-disalicylidene-1,2-cyclohexanediamine)SbF$_6$ and 60 mg of Co(N, N'-disalicylidene-1, 2-cyclohexanediamine)Cl, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst II-A.

Example II-2

1.0 g of SBA-6 was weighed and placed in 4 mL of a mixed solution of ethanol and dichloromethane containing 100 mg of Co(N,N'-bis (3,5-di-t-butyl salicylidene)-1,2-cyclohexanediamine)SbF$_6$ and 200 mg of Fe (N, N'-disalicylidene-1, 3-cyclohexanediamine)F, sealed and stirred for 3 h at 20° C., and then stirred with exposure to the ambient at 40° C. until the solvent was evaporated out. Prehydrolyzed ethyl orthosilicate was added, and stirred for 60 min. Ethanol was added, centrifugally separated, fully washed, and dried to obtain catalyst II-B.

Example II-3

1.0 g of SBA-16 was weighed and placed in 6 mL of methanol solution containing 300 mg of Ga (N,N'-disalicylidene-1,2-cycloethylenediamine)$SbF_6$ and 100 mg Al (N,N'-bis (3-t-butyl salicylidene)-1,2-cycloethylenediamine)Br, sealed and stirred for 4 h at 20° C., and then stirred with exposure to the ambient at 30° C. until the solvent was evaporated out. Prehydrolyzed ethyl orthosilicate was added, and stirred for 60 min. Ethanol was added, centrifugally separated, fully washed, and dried to obtain catalyst II-C.

Example II-4

1.0 g of FDU-1 was weighed and placed in 8 mL of a mixed solution of methanol and ethanol containing 300 mg of Fe(N,N'-disalicylidene-1,2-cycloethylenediamine)$SbF_6$ and 200 mg Cr(N,N'-bis(5-t-butyl salicylidene)-1,2-cycloethylenediamine)I, sealed and stirred for 4 h at 30° C., and then stirred with exposure to the ambient at 40° C. until the solvent was evaporated out. 2 ml toluene, 2 mg para-toluenesulfonic acid and 20 mmol trimethoxy propyl silane were added, refluxed overnight, centrifugally separated, fully washed, and dried to obtain catalyst II-D.

Comparative Example II-1

1.0 g of FDU-12 was weighed and placed in 4 mL of dichloromethane solution containing 100 mg of Co(N,N'-disalicylidene-1,2-cyclohexanediamine)$SbF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst II-E.

Comparative Example II-2

1.0 g of FDU-12 was weighed and placed in 4 mL of dichloromethane solution containing 100 mg of Co(N,N'-disalicylidene-1,2-cycloethylenediamine)Cl, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst II-F.

Example II-5

1.32 g of ethylene oxide was weighed, and the performance of the catalyst II-A was evaluated under the conditions of a temperature of 20° C., a pressure of 1.0 MPa, a water ratio of 2:1, a molar ratio of the catalyst to the ethylene oxide of 1:1000 and a reaction duration of 7 h. The results were shown in a table II-1.

Example II-6

The catalyst having been used once was recovered from example II-5, and was evaluated for its catalytic performance without activation regeneration under the same catalytic conditions as in example II-5. The results were shown in Table II-1.

Example II-7

The catalyst having been used twice was recovered from example II-6, and was evaluated for its catalytic performance without activation regeneration under the same catalytic conditions as in examples II-5 and 6. The results were shown in Table II-1.

Example II-8

1.32 g of ethylene oxide was weighed, and the performance of the catalyst II-B was evaluated under the conditions of a temperature of 20° C., a pressure of 1.0 MPa, a water ratio of 2:1, a molar ratio of the catalyst to the ethylene oxide of 1:1000 and a reaction duration of 7 h. The results were shown in a table II-1.

Example II-9

The catalyst having been used once was recovered from example II-8, and was evaluated for its catalytic performance without activation regeneration under the same catalytic conditions as in example II-8. The results were shown in Table II-1.

Example II-10

The catalyst having been used twice was recovered from example II-8, and was evaluated for its catalytic performance without activation regeneration under the same catalytic conditions as in examples II-8 and 9. The results were shown in Table II-1.

TABLE II-1

| Catalyst | Recycling performance of catalysts II-A and II-B | | |
|---|---|---|---|
| | Yield of ethylene glycol, first use (%) | Yield of ethylene glycol, 1 recycle (%) | Yield of ethylene glycol, 2 recycles (%) |
| II-A | 95 | 90 | 84 |
| II-B | 93 | 88 | 81 |

Example II-11

1.32 g of ethylene oxide was weighed, and the performance of the catalyst II-C was evaluated under the conditions of a temperature of 40° C., a pressure of 1.0 MPa, a water ratio of 6:1, a molar ratio of the catalyst to the ethylene oxide of 1:500 and a reaction duration of 4 h. The results were shown in a table II-2.

Example II-12

The catalyst having been used once was recovered from example II-11, and was evaluated for its catalytic performance without activation regeneration under the same catalytic conditions as in example II-11. The results were shown in Table II-2.

Example II-13

The catalyst having been used twice was recovered from example II-12, and was evaluated for its catalytic performance without activation regeneration under the same catalytic conditions as in examples II-11 and 12. The results were shown in Table II-2.

Example II-14

1.32 g of ethylene oxide was weighed, and the performance of the catalyst II-D was evaluated under the conditions of a temperature of 40° C., a pressure of 1.0 MPa, a water ratio of 6:1, a molar ratio of the catalyst to the ethylene oxide of 1:500 and a reaction duration of 4 h. The results were shown in a table II-2.

Example II-15

The catalyst having been used once was recovered from example II-14, and was evaluated for its catalytic performance without activation regeneration under the same catalytic conditions as in example II-14. The results were shown in Table II-2.

Example II-16

The catalyst having been used twice was recovered from example II-15, and was evaluated for its catalytic performance without activation regeneration under the same catalytic conditions as in examples II-14 and 15. The results were shown in Table II-2.

TABLE II-2

Recycling performance of catalysts II-C and II-D

| Catalyst | Yield of ethylene glycol, first use (%) | Yield of ethylene glycol, 1 recycle (%) | Yield of ethylene glycol, 2 recycles (%) |
|---|---|---|---|
| II-C | 94 | 89 | 83 |
| II-D | 93 | 87 | 80 |

Example II-17

1.74 g of propylene oxide was weighed, and the performance of the catalyst II-C was evaluated under the conditions of a temperature of 40° C., a pressure of 1.0 MPa, a water ratio of 2:1, a molar ratio of the catalyst to the propylene oxide of 1:1000 and a reaction duration of 7 h. The results were shown in a table II-3.

Example II-18

The catalyst having been used once was recovered from example II-17, and was evaluated for its catalytic performance without activation regeneration under the same catalytic conditions as in example II-17. The results were shown in Table II-3.

Example II-19

The catalyst having been used twice was recovered from example II-18, and was evaluated for its catalytic performance without activation regeneration under the same catalytic conditions as in examples II-17 and 18. The results were shown in Table II-3.

Example II-20

1.74 g of propylene oxide was weighed, and the performance of the catalyst II-D was evaluated under the conditions of a temperature of 40° C., a pressure of 1.0 MPa, a water ratio of 2:1, a molar ratio of the catalyst to the propylene oxide of 1:1000 and a reaction duration of 7 h. The results were shown in a Table II-3.

Example II-21

The catalyst having been used once was recovered from example II-20, and was evaluated for its catalytic performance without activation regeneration under the same catalytic conditions as in example II-20. The results were shown in Table II-3.

Example II-22

The catalyst having been used twice was recovered from example II-21, and was evaluated for its catalytic performance without activation regeneration under the same catalytic conditions as in examples II-21 and 22. The results were shown in Table II-3.

TABLE II-3

Recycling performance of catalysts II-C and II-D

| Catalyst | Yield of propylene glycol, first use (%) | Yield of propylene glycol, 1 recycle (%) | Yield of propylene glycol, 2 recycles (%) |
|---|---|---|---|
| II-C | 92 | 87 | 81 |
| II-D | 91 | 85 | 79 |

Example II-23

1.74 g of propylene oxide was weighed, and the performance of the catalyst II-A was evaluated under the conditions of a temperature of 40° C., a pressure of 1.0 MPa, a water ratio of 8:1, a molar ratio of the catalyst to the propylene oxide of 1:500 and a reaction duration of 4 h. The results were shown in a table II-4.

Example II-24

The catalyst having been used once was recovered from example II-23, and was evaluated for its catalytic performance without activation regeneration under the same catalytic conditions as in example II-23. The results were shown in Table II-4.

Example II-25

The catalyst having been used twice was recovered from example II-24, and was evaluated for its catalytic performance without activation regeneration under the same catalytic conditions as in examples II-23 and 24. The results were shown in Table II-4.

Example II-26

1.74 g of propylene oxide was weighed, and the performance of the catalyst II-B was evaluated under the conditions of a temperature of 40° C., a pressure of 1.0 MPa, a water ratio of 8:1, a molar ratio of the catalyst to the propylene oxide of 1:500 and a reaction duration of 4 h. The results were shown in a table II-4.

Example II-27

The catalyst having been used once was recovered from example II-26, and was evaluated for its catalytic performance without activation regeneration under the same catalytic conditions as in example II-26. The results were shown in Table II-4.

Example II-28

The catalyst having been used twice was recovered from example II-27, and was evaluated for its catalytic performance without activation regeneration under the same catalytic conditions as in examples II-26 and 27. The results were shown in Table II-4.

TABLE II-4

Recycling performance of catalysts II-A and II-B

| Catalyst | Yield of propylene glycol, first use (%) | Yield of propylene glycol, 1 recycle (%) | Yield of propylene glycol, 2 recycles (%) |
|---|---|---|---|
| II-A | 94 | 89 | 83 |
| II-B | 93 | 87 | 81 |

Comparative Example II-3

1.32 g of ethylene oxide was weighed, and the performance of the catalyst II-E was evaluated under the conditions of a temperature of 20° C., a pressure of 1.0 MPa, a water ratio of 2:1, a molar ratio of the catalyst to the ethylene oxide of 1:1000 and a reaction duration of 7 h. The results were shown in a table II-5.

Comparative Example II-4

1.32 g of ethylene oxide was weighed, and the performance of the catalyst II-F was evaluated under the conditions of a temperature of 20° C., a pressure of 1.0 MPa, a water ratio of 2:1, a molar ratio of the catalyst to the ethylene oxide of 1:1000 and a reaction duration of 7 h. The results were shown in a table II-5.

TABLE II-5

Performance of catalysts II-E and II-F

| Catalyst | Yield of ethylene glycol, first use (%) |
|---|---|
| II-E | 12 |
| II-F | 63 |

Example III-1

0.50 g of F127, 0.6 g of mesitylene and 2.5 g of KCl were weighed and dissolved in 30 mL of 2M HCl aqueous solution at a temperature of 16° C., and stirred for 2 hours; 2.08 g TEOS was added, stirring was continued for 24 h at 16° C. and then hydrothermal treatment was carried out in an oven at 100° C. for 24 h. Taken out, washed, dried, and calcinated at 550° C. for 6 h to obtain the nanocage substrate material FDU-12. 0.331 g of ferrocene hexafluorophosphate and 0.492 g of Co(N,N'-disalicylidene-1,2-hexanaphthene diamine) were weighed, dissolved in a mixed solution of 15 mL dichloromethane and 15 mL acetonitrile, and stirred at room temperature for 12 h with exposure to the ambient, solvent was removed by spinning, and fully washed with n-hexane and dried, to obtain the active center Co(N,N'-disalicylidene-1,2-hexanaphthene diamine)$PF_6$. 1.0 g of FDU-12 was weighed and placed in 6 mL of dichloromethane solution containing 100 mg of Co(N,N'-disalicylidene-1,2-cyclohexanediamine)$PF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-A.

Example III-2

1.0 g of SBA-6 was weighed and placed in 6 mL of dichloromethane solution containing 100 mg of Fe(N,N'-bis (3,5-di-t-butyl salicylidene)-1,2-cycloethylenediamine)$PF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-B.

Example III-3

1.0 g of SBA-16 was weighed and placed in 6 mL of dichloromethane solution containing 100 mg of Ga(N,N'-disalicylidene-1,2-cyclohexanediamine)$PF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-C.

Example III-4

1.0 g of FDU-1 was weighed and placed in 6 mL of dichloromethane solution containing 100 mg of Al(N,N'-bis (3-t-butyl salicylidene)-1,2-cycloethylenediamine)$PF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-D.

Example III-5

1.0 g of KIT-5 was weighed and placed in 6 mL of dichloromethane solution containing 100 mg of Cr(N,N'-bis (5-t-butyl salicylidene)-1,2-cyclohexanediamine)$PF_6$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-E.

Example III-6

1.0 g of SBA-16 was weighed and placed in 6 mL of dichloromethane solution containing 100 mg of Co(N,N'-disalicylidene-1,2-cyclohexanediamine)$BF_4$, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-F.

Comparative Example III-1

1.0 g of SBA-16 was weighed and placed in 6 mL of dichloromethane solution containing 100 mg of Co(N,N'-disalicylidene-1,2-cyclohexanediamine)OTs, sealed and stirred for 2 h at 20° C., and then stirred with exposure to the ambient at 20° C. until the solvent was evaporated out. Prehydrolyzed methyl orthosilicate was added, and stirred for 40 min. Ethanol was added, centrifugally separated, fully washed, and dried to obtain catalyst III-G.

Examples III-7~15

1.32 g of ethylene oxide was weighed, and the performance of the catalyst III-A, III-B and III-C was evaluated under the conditions of a temperature of 20° C., a pressure of 1.0 MPa, a water ratio of 2:1, a molar ratio of the catalyst to the ethylene oxide of 1:1000 and a reaction duration of 7 h. The catalysts III-A, III-B and III-C having been used were recovered, and were used for the following catalytic reactions (thus recycled twice) without activation regeneration under the same catalytic conditions. The results were shown in Table III-1.

TABLE III-1

Recycling performance of catalysts III-A, III-B, and III-C

| Catalyst | Yield of ethylene glycol, first use (%) | Yield of ethylene glycol, 1 recycle (%) | Yield of ethylene glycol, 2 recycles (%) |
|---|---|---|---|
| III-A | ≥97 | ≥94 | ≥89 |
| III-B | ≥96 | ≥93 | ≥88 |
| III-C | ≥96 | ≥93 | ≥87 |

Examples III-16~24

1.32 g of ethylene oxide was weighed, and the performance of the catalyst III-D, III-E and III-F were evaluated under the conditions of a temperature of 40° C., a pressure of 1.0 MPa, a water ratio of 6:1, a molar ratio of the catalyst to the ethylene oxide of 1:500 and a reaction duration of 4 h. The catalysts III-D, III-E and III-F having been used were recovered, and were used for the following catalytic reactions (thus recycled twice) without activation regeneration under the same catalytic conditions. The results were shown in Table III-2.

TABLE III-2

Recycling performance of catalysts III-D, III-E, and III-F

| Catalyst | Yield of ethylene glycol, first use (%) | Yield of ethylene glycol, 1 recycle (%) | Yield of ethylene glycol, 2 recycles (%) |
|---|---|---|---|
| III-D | ≥95 | ≥92 | ≥85 |
| III-E | ≥94 | ≥91 | ≥84 |
| III-F | ≥95 | ≥92 | ≥86 |

Examples III-25~33

1.74 g of propylene oxide was weighed, and the performance of the catalyst III-D, III-E and III-F were evaluated under the conditions of a temperature of 40° C., a pressure of 1.0 MPa, a water ratio of 2:1, a molar ratio of the catalyst to the propylene oxide of 1:1000 and a reaction duration of 7 h. The catalysts III-D, III-E and III-F having been used were recovered, and were used for the following catalytic reactions (thus recycled twice) without activation regeneration under the same catalytic conditions. The results were shown in Table III-3.

TABLE III-3

Recycling performance of catalysts III-D, III-E, and III-F

| Catalyst | Yield of propylene glycol, first use (%) | Yield of propylene glycol, 1 recycle (%) | Yield of propylene glycol, 2 recycles (%) |
|---|---|---|---|
| III-D | ≥94 | ≥91 | ≥83 |
| III-E | ≥93 | ≥90 | ≥83 |
| III-F | ≥94 | ≥90 | ≥84 |

Examples III-34~42

1.74 g of propylene oxide was weighed, and the performance of the catalyst III-A, III-B and III-C were evaluated under the conditions of a temperature of 60° C., a pressure of 1.0 MPa, a water ratio of 8:1, a molar ratio of the catalyst to the propylene oxide of 1:500 and a reaction duration of 4 h. The catalysts III-A, III-B and III-C having been used were recovered through centrifugation, and were respectively used for the next catalytic reaction (thus recycled twice) without activation regeneration under the same catalytic conditions. The results were shown in Table III-4.

TABLE III-4

Recycling performance of catalysts III-A, III-B, and III-C

| Catalyst | Yield of propylene glycol, first use (%) | Yield of propylene glycol, 1 recycle (%) | Yield of propylene glycol, 2 recycles (%) |
|---|---|---|---|
| III-A | ≥96 | ≥93 | ≥88 |
| III-B | ≥95 | ≥92 | ≥86 |
| III-C | ≥95 | ≥93 | ≥87 |

Comparative Examples III-2~3

1.32 g of ethylene oxide was weighed and the performance of active centers Co(N,N'-disalicylidene-1,2-cyclohexanediamine)PF$_6$ and Co(N,N'-disalicylidene-1,2-cyclohexanediamine)OTs used as homogeneous catalyst were evaluated under conditions of a temperature of 20° C., a pressure of 1.0 MPa, a water ratio of 2:1, a molar ratio of the catalyst to the ethylene oxide of 1:1000 and a reaction duration of 7 h. The results were shown in Table III-5.

TABLE III-5

Performance of active centers Co(N,N'-disalicylidene-1,2-cyclohexanediamine)PF$_6$ and Co(N,N'-disalicylidene-1,2-cyclohexanediamine)OTs used as homogeneous catalysts

| Catalyst | Yield of ethylene glycol (%) |
|---|---|
| Co(N,N'-disalicylidene-1,2-cyclohexanediamine)PF$_6$ | ≥85 |
| Co(N,N'-disalicylidene-1,2-cyclohexanediamine)OTs | ≥92 |

Comparative Example III-4

1.32 g of ethylene oxide was weighed, and the performance of the catalyst III-G was evaluated under the conditions of a temperature of 20° C., a pressure of 1.0 MPa, a water ratio of 2:1, a molar ratio of the catalyst to the ethylene oxide of 1:1000 and a reaction duration of 7 h. The catalyst III-G having been used were recovered through centrifugation, and was used for the next catalytic reaction (thus recycled twice) without activation regeneration under the same catalytic conditions. The results were shown in Table III-4.

TABLE III-6

Recycling performance of catalyst III-G

| Catalyst | Yield of ethylene glycol, first use (%) | Yield of ethylene glycol, 1 recycle (%) |
|---|---|---|
| III-G | ≥97 | ≥45 |

The invention claimed is:

1. A nanocage-confined catalyst, having an active center of formula (I-1) and/or an active center of formula (I-2):

$$M(Salen1)X \quad (I\text{-}1),$$

$$M'(Salen2) \quad (I\text{-}2),$$

such that the catalyst has formula (I):

$$NC\text{-}m[M(Salen1)X]\text{-}n[M'(Salen2)] \quad (I),$$

wherein:
NC is a material having a nanocage structure and is selected from mesoporous silica nanoparticles having a nanocage structure or organic hybrid mesoporous silica nanoparticles having a nanocage structure,
each occurrence of M is independently selected from the group consisting of Co ion, Fe ion, Ga ion, Al ion, Cr ion, and a mixture thereof; and each occurrence of M' is independently selected from Cu ion, Ni ion and a mixture thereof;
m is an integer of 0 to 10, n is an integer of 0 to 5; provided that at least one of m and n is not 0;
each occurrence of Salen1 and Salen2 is independently a derivative of a Shiff base, wherein the derivative of Schiff base is N,N'-disalicylidene-1,2-cyclohexanediamine or a substituted N,N'-disalicylidene-1,2-cyclohexanediamine;
X is an axial anion, wherein each occurrence of X is independently selected from the group consisting of unsubstituted acetate, unsubstituted benzenesulfonate, unsubstituted benzoate, $F^-$, $Cl^-$, $Br^-$, $I^-$, $SbF_6^-$, $PF_6^-$, $BF_4^-$ and a mixture thereof; with provisos that:
when X is unsubstituted acetate, unsubstituted benzenesulfonate, or unsubstituted benzoate, then M is not a Co ion, and when X is $F^-$, $Cl^-$, $Br^-$, or $I^-$, then m is not less than 2, and at least one occurrence of X in formula (I-1) is $SbF_6^-$.

2. The catalyst according to claim 1, wherein each occurrence of M in formula (I-1) is independently selected from $Co^-$, $Fe^-$, $Ga^-$, $Al^-$, $Cr^-$ and a mixture thereof, and/or each occurrence of M' in formula (I-2) is independently selected from $Cu^-$, $Ni^-$ and a mixture thereof.

3. The catalyst according to claim 1, wherein m is 0 to 5.
4. The catalyst according to claim 1, wherein n is 0 to 3.
5. The catalyst according to claim 1, wherein m is 0-2 and n is 0-1.
6. The catalyst according to claim 1, wherein m is 1, n is 0, and X is selected from the group consisting of unsubstituted acetate, unsubstituted benzenesulfonate, unsubstituted benzoate, $SbF_6^-$, $PF_6^-$, and $BF_4^-$.

7. The catalyst according to claim 1, wherein m is 2, n is 0 to 1, and each occurrence of M(Salen1)X of formula (I-1) is different, the catalyst is of formula (II):

$$NC\text{-}[M(Salen1)X]\text{-}[M(Salen1)X]\text{-}n[M'(Salen2)] \quad (II); \text{ or}$$

m is 2, n is 0, and each occurrence of M(Salen1)X is different, the catalyst is of formula (II-1);

$$NC\text{-}[M(Salen1)X]\text{-}[M(Salen1)X] \quad (II\text{-}1),$$

in formula (II) or (II-1), each occurrence of M is different and independently selected from $Co^{3+}$, $Fe^{3+}$, $Ga^{3+}$, $Al^{3+}$, and $Cr^{3+}$, and each Salen1 is same or different.

8. The catalyst according to claim 7, wherein one occurrence of X is $SbF_6^-$, and the other occurrence of X is $F^-$, $Cl^-$, $Br^-$ or $I^-$.

9. The catalyst according to claim 1, wherein m is 2 or more, and each occurrence of M(Salen1)X in formula (I-1) is different from one another.

10. The catalyst according to claim 1, wherein n is 2 or more, and each occurrence of M'(Salen2) in formula (I-2) is different from one another.

11. The catalyst according to claim 1, wherein NC is selected from SBA-6, SBA-16, FDU-1, FDU-12, KIT-5, and AMS-8.

12. A nanocage-confined catalyst having formula (II-3):

$$NC\text{-}[Co(Salen1)SbF_6\text{-}M(Salen1)X] \quad (II\text{-}3),$$

wherein NC and Salen1 are each independently as defined in claim 1; X is selected from $F^-$, $Cl^-$, $Br^-$, and $I^-$; and M is selected from $Co^{3+}$, $Fe^{3+}$, $Ga^{3+}$, $Al^{3+}$ and $Cr^{3+}$.

13. A nanocage-confined catalyst having formula (II-4):

$$NC\text{-}[M(Salen1)SbF_6\text{-}Co(Salen1)X] \quad (II\text{-}4),$$

wherein NC and Salen1 are each independently as defined in claim 1; X is selected from $F^-$, $Cl^-$, $Br^-$, and $I^-$; and M is selected from $Co^{3+}$, $Fe^{3+}$, $Ga^{3+}$, $Al^{3+}$ and $Cr^{3+}$.

14. A nanocage-confined catalyst having formula (III-1) or (III-2):

$$NC\text{-}[Co(Salen1)PF_6] \quad (III\text{-}1), \text{ or}$$

$$NC\text{-}[Co(Salen1)BF_4] \quad (III\text{-}2),$$

wherein NC and Salen1 are each independently as defined in claim 1.

15. A process of preparing the nanocage-confined catalyst of claim 1, comprising the steps of:
adding an active center M(Salen1)X or M'(Salen2) and a nanocage material NC into a solvent, and stirring; removing the solvent; and encapsulating, to obtain the nanocage-confined catalyst.

16. The process according to claim 15, characterized in that M comprises $Fe^{3+}$, $Ga^{3+}$, $Al^{3+}$, and $Cr^{3+}$, M' comprises $Cu^{2+}$ and $Ni^2$; Salen1 and Salen2 are respectively a Shiff base derivative, X is an axial anion, and the X comprises acetate, benzene sulfonate, benzoate, substituted acetate, substituted benzene sulfonate, substituted benzoate, $F^-$, $Cl^-$, $Br^-$, $I^-$, $SbF_6^-$, $PF_6^-$, and $BF_4^-$.

17. The process according to claim 15, characterized in that the solvent comprises at least one of dichloromethane, ethanol, and methanol.

18. A method for producing glycol, comprising hydration of alkylene oxide in the presence of the nanocage-confined catalyst of claim 1.

19. The nanocage-confined catalyst of claim 1, wherein both m and n are not 0.

* * * * *